United States Patent
Wu et al.

(10) Patent No.: US 8,376,784 B2
(45) Date of Patent: Feb. 19, 2013

(54) CONNECTOR AND BIOSENSING METER WITH THE CONNECTOR

(75) Inventors: Chia-Chi Wu, Kaohsiung (TW); Wen-Jung Huang, Luzhu Township, Taoyuan County (TW); Yi-Hsin Huang, Taipei (TW); Hui-Sheng Hou, Luzhou (TW); Chao-Wang Chen, Taipei (TW)

(73) Assignee: Taidoc Technology Corporation, Taipei County (TW)

( * ) Notice: Subject to any disclaimer, the term of this patent is extended or adjusted under 35 U.S.C. 154(b) by 211 days.

(21) Appl. No.: 12/961,658

(22) Filed: Dec. 7, 2010

(65) Prior Publication Data

US 2011/0143562 A1 Jun. 16, 2011

(30) Foreign Application Priority Data

Dec. 14, 2009 (TW) ................................ 98142806 A

(51) Int. Cl.
*H01R 24/00* (2006.01)
*H01R 33/00* (2006.01)

(52) U.S. Cl. ...................................... 439/660; 439/909

(58) Field of Classification Search .................. 439/912, 439/77, 629, 152, 159, 637, 909, 660; 600/345, 600/573
See application file for complete search history.

(56) References Cited

U.S. PATENT DOCUMENTS

| 5,580,257 | A  | * | 12/1996 | Harwath    | 439/108 |
| 5,634,819 | A  | * | 6/1997  | Pan et al. | 439/637 |
| 5,820,392 | A  | * | 10/1998 | Lin et al. | 439/108 |
| 5,997,312 | A  | * | 12/1999 | Ho et al.  | 439/60  |
| 6,652,322 | B2 | * | 11/2003 | Ito et al. | 439/637 |
| 7,607,949 | B2 | * | 10/2009 | Hsu        | 439/637 |
| 8,113,887 | B2 | * | 2/2012  | Osawa et al. | 439/637 |
| 8,187,038 | B2 | * | 5/2012  | Kamiya et al. | 439/637 |

* cited by examiner

*Primary Examiner* — Hae Moon Hyeon
(74) *Attorney, Agent, or Firm* — Chun Ming Shih

(57) ABSTRACT

The present invention related to a connector which is used in a biosensing meter and receives an insertion, comprising a body and a plurality of terminal components. The plurality of terminals arranged all around and face to face, thereby reducing the volume of the connector. Furthermore, the plurality of terminal respectively contact the insertion equally thereby increasing the transmissible accuracy and the determination accuracy. The connector can further comprise a sliding base connected with the body for ejecting the insertion, whereby the invented connector can achieve multi-functional goal.

24 Claims, 6 Drawing Sheets

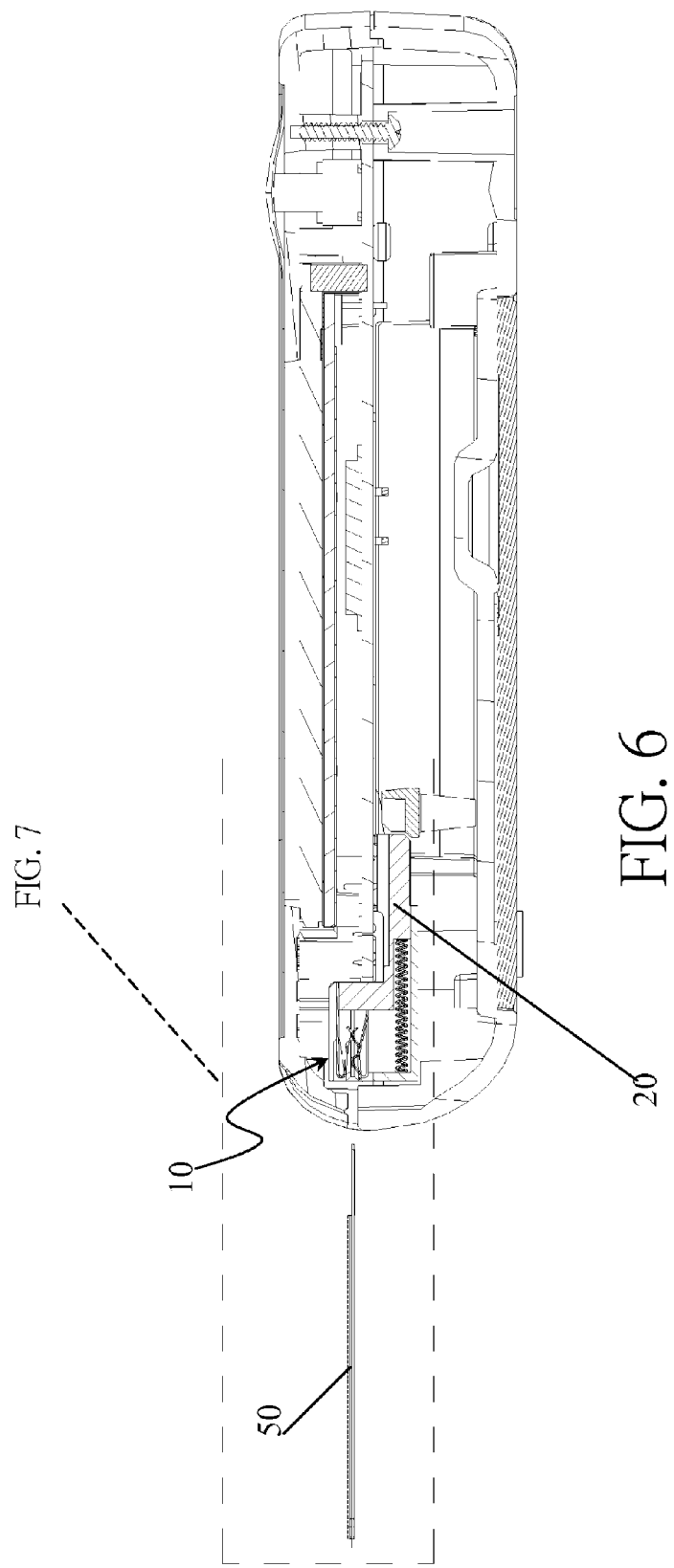

CONNECTOR AND BIOSENSING METER WITH THE CONNECTOR

BACKGROUND OF THE INVENTION

1. Field of the Invention

The present invention generally relates to a connector and a biosensing meter with the connector, in particular, to a connector which is used to receive a corresponding strip has a plurality of terminal components arranged specially, whereby size may be reduced and the transmissible accuracy and the determination accuracy may be increased.

2. Description of Related Art

With advances in technology and changes in living habits, examinations that must be tested in the hospital in the past, and now at home. Specially, changes in lifestyle caused the increase in chronic disease patients, but also accelerated the development of the medical industry. Blood glucose test item is one of important measurements. Measuring and monitoring blood glucose are important steps to prevent the complications of diabetes.

Current market selling biosensor device can be used to measure analytes of the liquid, further can be used to measure cholesterol, uric acid, protein, glucose, glycated hemoglobin, etc., of biologic sample, wherein the sample may be whole blood, plasma, serum, urine, tissue fluid, etc., by the electrochemical biosensor strip and biosensing meter with which to measure. The biosensing meter includes a connector for receiving the electrochemical biosensor strip, and electrodes of the electrochemical biosensor strip can be electrical connect to the biosensing meter through the connector.

Conventional connector includes a body. The body has an opening. Terminal components of the connector are located in the inner of the opening. The terminal components are arranged with equidistance on a plane. When the electrochemical biosensor strip is inserted into the opening, the terminal components are connected to the electrodes of the electrochemical biosensor strip. It should noted, the electrodes of the electrochemical biosensor strip are scratched easily by the terminal components of the conventional connector. Further, the electrodes are disposed on the upper plane of the electrochemical biosensor strip. When the electrodes are connected to the conventional connector, the electrodes are pushed from top to down by the terminal components. The push may be not uniform, and the connection between the electrodes and the terminal components may be abnormal. In addition, in response to market demand decreasingly amount of sample, the size of the electrochemical biosensor strips are designed in different needs of different size, but limited to the conventional structure and alignment with the terminal design, the conventional connector can not achieve these requirements. In other words, the conventional connector does not have variable characteristics.

To sum up the lack of conventional connector as a reference for manufacturers to improve, how to change or reduce the size of the connector to match the biosensing meter and the electrochemical biosensor test strip.

SUMMARY OF THE INVENTION

Accordingly, the present invention provides a connector. The connector is used in a biosensing meter to reduce the meter volume. The connector is adapted to an electrochemical biosensor strip having complex electrode structure, so as to achieve the purpose of the average force. Further, in an embodiment of the present invention, the connector further has a function for ejecting the strip, so that another one ejecting unit may be unnecessary and the meter volume may be reduced.

Accordingly, a connector of the present invention comprises a body and a plurality of terminal components. A connector is used in a biosensing meter. The biosensing meter is used to receive an insertion. The body comprises a terminal assembly opening and an insertion port. The terminal assembly opening is located in a terminal of the body, and the insertion port is located in another terminal of the body and is used to receive the insertion. In an embodiment of the present invention, the insertion port shows a transverse opening. The width of the transverse opening is less than 8.5 mm. For example, the width of the transverse opening may be 8.5 mm, 7.5 mm or 7.0 mm. The terminal components are assembled in the terminal assembly opening of the body. A terminal of each of the terminal components has a contact point, the contact point is used to contact to the insertion, the contact points are arranged from left to right, and the contact points are arranged from top to bottom. In an embodiment of the present invention, the contact points are arranged from front to back.

In addition, the connector further comprises a sliding base. The body further comprises a sliding base assembly opening. The sliding base assembly opening is located below the terminal assembly opening, and the sliding base is slidely assembled in the sliding base assembly opening of the body. In an embodiment of the present invention, the sliding base assembly opening is extended from the bottom of the terminal assembly opening to the top and the sliding base assembly opening includes a pushrod assembly opening located in a side of the terminal assembly opening. In the preferred embodiment of the present invention, the sliding base includes a pushrod and the pushrod is located in a terminal of the sliding base and extended to the top and assembled in the pushrod assembly opening. In another embodiment of the present invention, the pushrod assembly opening is located two sides of the terminal assembly opening and the sliding base comprises two pushrods, and the pushrods are respectively located in two sides of the terminal of the sliding base and assembled in the pushrod assembly opening.

In an embodiment of the present invention, the sliding base assembly opening further includes a block located in appropriate inside thereof, and the sliding base includes a bump. The bump is disposed and protruding in a side of the sliding base to prop up the block of the sliding base assembly opening. In other embodiment of the present invention, two blocks are respectively located in two inner side surfaces of the sliding base assembly opening, the sliding base includes two bumps, and the bumps are respectively disposed and protruding in two sides of the sliding base. In another embodiment of the present invention, the bump is extended to outside to form a flange, and the flange is used to engage and prevent the sliding base from being separated from the body. Furthermore, in one embodiment of the present invention, the flange is an inclination type, the flange includes a slanting surface, and the slanting surface is used to help the sliding base be assembled into the body.

In an embodiment of the present invention, the terminal component comprises a first type terminal component, a second type terminal component, a third type terminal component, and a fourth type terminal component. The first type terminal component has a terminal bended downward to form a contact point, and a bending area is formed in front terminal of the contact point. The second type terminal component has a terminal bended downward to form a contact point. The third type terminal component has a terminal bended upward to form a contact point, and a bending area is formed in front terminal of the contact point. The fourth type terminal component has a terminal bended upward to form a contact point.

In an embodiment of the present invention, the terminal components comprise three first type terminal components, two second type terminal components, two third type terminal components and two fourth type terminal components.

In an embodiment of the present invention, a plurality of grooves are located in the terminal assembly opening, the grooves is used to assemble with the terminal components. In another embodiment of the present invention, the contact points of the terminal components show an inverted R angle to avoid that a contact area of the insertion is scratched easily by the contact points. In other embodiment of the present invention, a bending area of the terminal components has elasticity and shows U shape.

In the said connector of an embodiment of the present invention, the terminal component is formed by a metal, the metal is bended to form two areas, the one area shows L shape, and the one area is extended from another side bending of the other area that have the contact point to another terminal. In another embodiment of the present invention, the terminal components include two terminal types. An L shape height of the one terminal type is more than that of the other terminal type. In other embodiment of the present invention, L shape heights of the first type terminal component and the second type terminal component are more than that of the third type terminal component and fourth type terminal component. Whereby, the first type terminal component and the second type terminal component may be extended from top to down to form the contact points, and the third type terminal component and fourth type terminal component may be extended from down to top to form the contact points In an embodiment of the present invention, a C angle area is located in a near terminal of the terminal components to enhance the soldering intensity. In other aspect, the contact point of the terminal components comprises a gold plating layer to extend the life of the terminal components. Further, a welding point is disposed in a terminal of the terminal component to weld to the PCB (printed circuit board) easily.

In an embodiment of the present invention, the biosensing meter is used to measure blood glucose, and the insertion may be an electrochemical biosensor strip. More particular, the electrochemical biosensor strip is used to measure blood glucose.

In an embodiment of the present invention, the connector further comprises an elastic component. The elastic component is assembled between the sliding base assembly opening of the body and the sliding base. The elastic component may be a spring.

In another aspect, the present invention provides a biosensing meter. The biosensing meter includes said connector and the corresponding electrochemical biosensor strip. The connector connects to the corresponding electrochemical biosensor strip selectively.

To sum up, the connector of the present invention may have small size, and may be adapted to the insertion having more functions. In addition, the connector of the present invention may further include a sliding base to have an ejecting function. According to the designs of the body, the terminal components and the sliding base, the connector may have small size and may be adapted to the insertion, particular to the electrochemical biosensor strip, having more functions.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 6 is a partial profile view of the biosensing meter with the connector according to FIG. 5.

DESCRIPTION OF THE EMBODIMENTS

Figure 2:
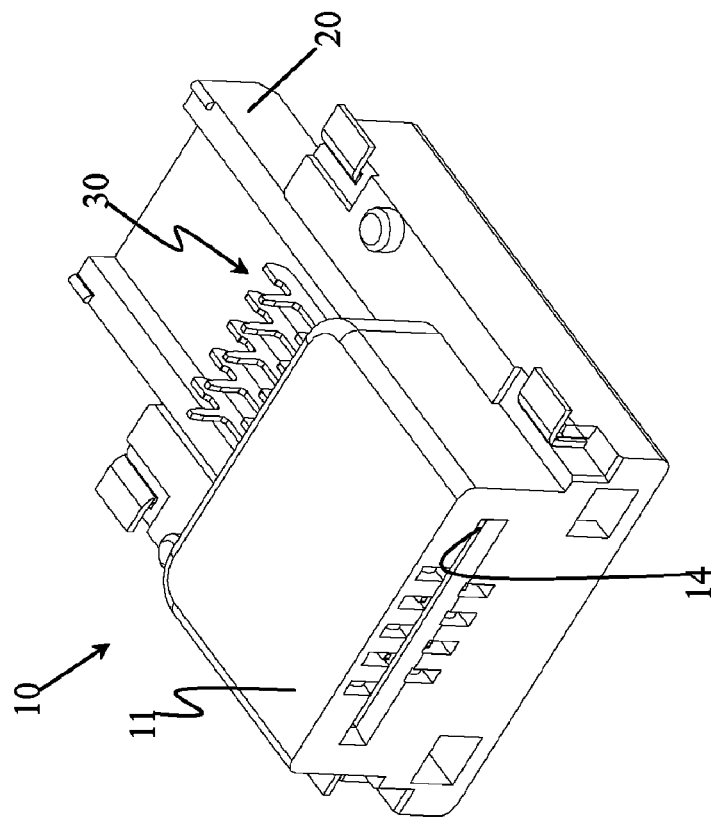
FIG. 2 is another schematic view of the connector according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

Figure 1:
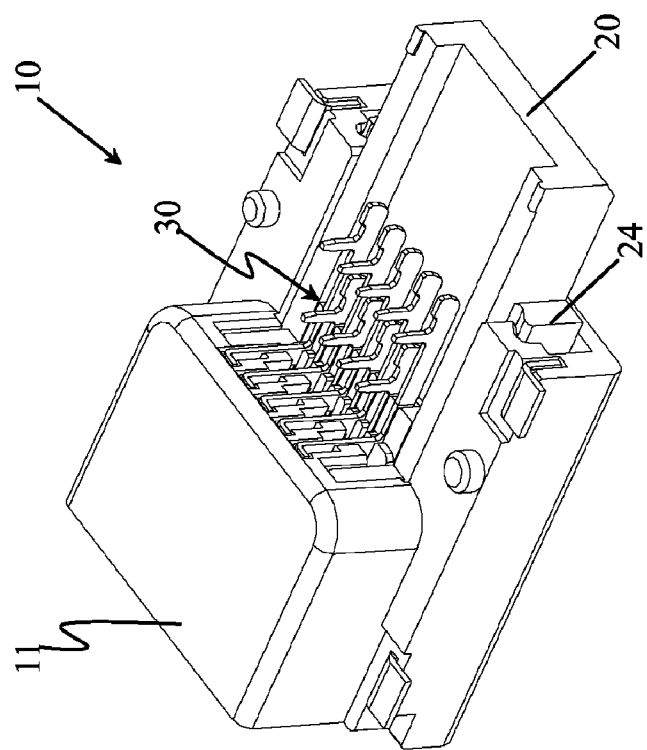
FIG. 1 is a schematic view of a connector according to an embodiment of the present invention.
Figure 3:
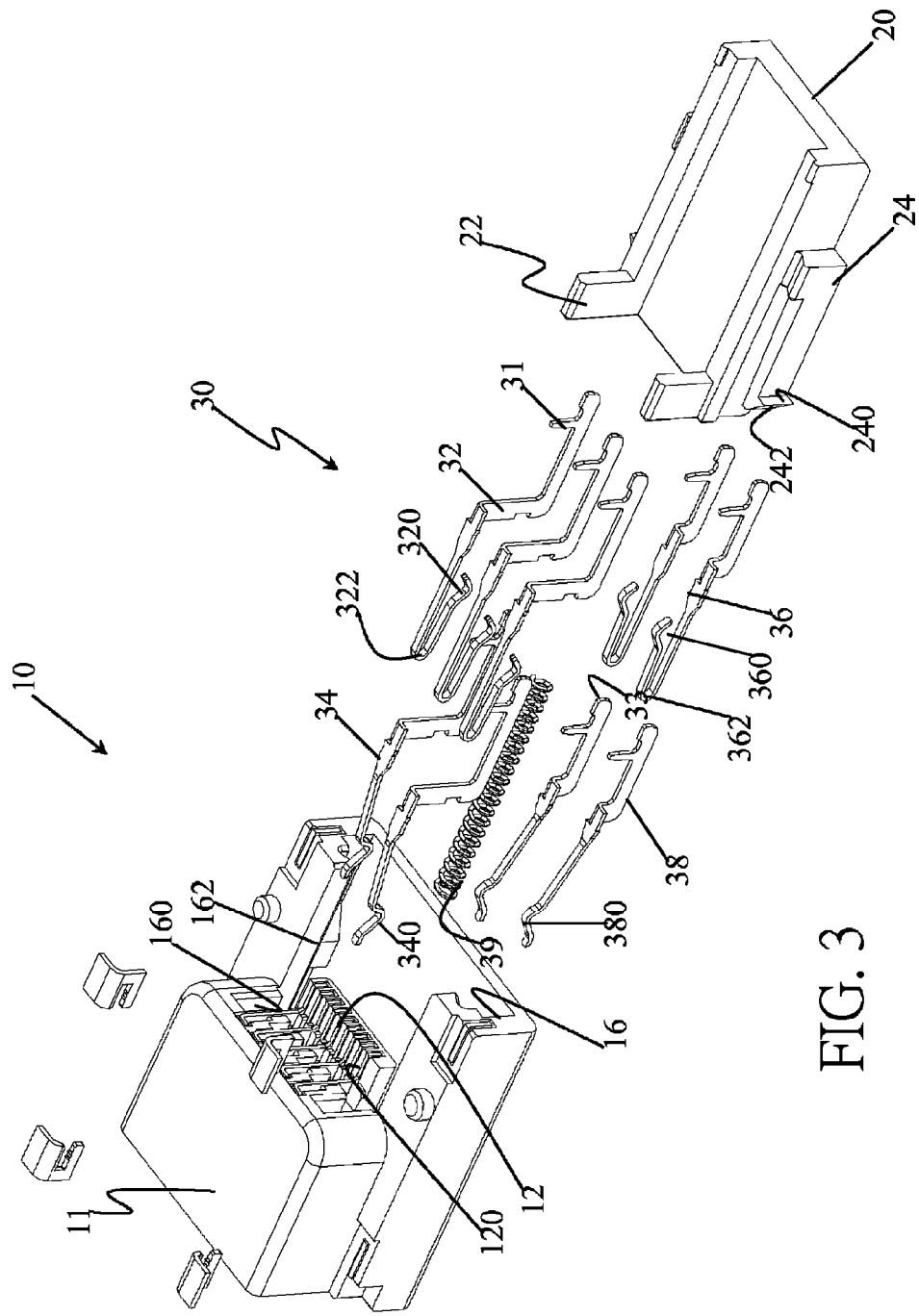
FIG. 3 is explosion diagram of the connector according to an embodiment of the present invention.

The present invention relates to a connector. Referring to FIG. 1 to FIG. 3. FIG. 1 and FIG. 2 are different schematic views of a connector according to an embodiment of the present invention. FIG. 3 is explosion diagram of the connector according to an embodiment of the present invention. The connector (10) includes an body (11), a sliding base (20) and a plurality of terminal components (30). The connector (10) may be used in a biosensing meter, and may be used to receive an insertion. The insertion may be electrochemical biosensor strip, for instance, the biosensing meter and the electrochemical biosensor strip are used to measure blood glucose.

The body (11) includes a terminal assembly opening (12), an insertion port (14) and a sliding base assembly opening (16), and has a proximal end and a distal end. The terminal assembly opening (12) is located in the proximal end of the body (11), and with a configuration of a plurality of terminal components (30), for instance, a plurality of groove (120) are disposed in the terminal assembly opening (12). Referring to FIG. 2, the insertion port (14) is disposed in the distal end of the body (11), and the insertion port (14) is opposite the terminal assembly opening (12), for instance, the insertion port (14) shows a transverse opening. Further, the width of the insertion port (14) may be less than 8.5 mm. The width of the insertion port (14) may be 8.5 mm, 7.5 mm or 7.0 mm. The sliding base assembly opening (16) is located below the terminal assembly opening (12), more specifically, the sliding base assembly opening (16) is extended from the bottom of the terminal assembly opening (12) to the top, the terminal assembly opening (12) includes a pushrod assembly opening (160) located in a side of the terminal assembly opening. Further, the sliding base assembly opening (16) further includes at least one block (162) located in appropriate inside thereof. In other embodiment, the sliding base assembly opening (16) may have two blocks (162) respectively located in two inner side surfaces thereof.

The sliding base (20) is assembled to the body (11). The sliding base (20) includes at least one pushrod (22) and at least one bump (24). The pushrod (22) is located in a terminal of the sliding base (20) and extended and protruded to the top. In other embodiment, the sliding base (20) may have two pushrods (22). The pushrods (22) are respectively located in two sides of the terminal of the sliding base (20). The bump (24) is disposed and protruding in a side of the sliding base (20). In other embodiment, the sliding base (20) may include two bumps (24). The two bumps (24) are respectively located in two side of the sliding base (20). Further, the bump (24) is extended to outside to form a flange (240), and the flange (240) is used to engage and prevent the sliding base (24) from being separated from the body (11). Furthermore, the flange (240) is an inclination type, the flange (240) includes a slanting surface (242), and the slanting surface (242) is used to help the sliding base (20) be assembled into the body (11). In addition, the flange (240) can be wedged to the block (162) of the sliding base assembly opening (16). When the sliding base (20) is assembled to the body (11), the bump (24) of the sliding base (20) is set into the sliding base assembly opening (16) of the body (11), and the pushrod (22) is set into the pushrod assembly opening (160).

The terminal components (30) are used to contact the insertion and set into the body (11), and the terminal components each has a proximal terminal and a distal terminal and the proximal terminal is assembled in the terminal assembly opening of the body. More specifically, a welding point (31) is disposed in the proximal terminal of the terminal component (30) to weld to the PCB (printed circuit board) easily. The terminal components (30) may include a first type terminal component (32), a second type terminal component (34), a third type terminal component (36), and a fourth type terminal component (38). The first type terminal component (32) has a terminal bended downward to form a contact point (320), and a bending area (322) is formed in front terminal of the contact point (320). The bending area (322) may have elasticity and show U shape. The second type terminal component (34) has a terminal bended downward to form a contact point (340). The third type terminal component (36) has a terminal bended upward to form a contact point (360), and a bending area (362) is formed in front terminal of the contact point (360). The bending area (362) may have elasticity and show U shape. The fourth type terminal component (38) has a terminal bended upward to form a contact point (380). An exterior corner respectively of the contact points (320,340, 360,380) may be a round.

In an embodiment of the present invention, the connector (10) includes at least four terminals, the contact points of the four terminals are arranged from front to back, so that the complexity of the insertion contact structure can be increased and the volume of insertion may not be increased. In another embodiment of the present invention, the connector (10) includes five terminals, and at least one terminal is disposed on a first plane and the others are disposed are disposed on a second plane contrasting to the first plane.

For instance, the contact points of the four terminals are designed downward, and the openings thereof are designed upward. The contact point of the other terminal is designed upward, and the opening thereof is designed downward. Whereby, electrodes of the electrochemical biosensor strip may be disposed on difference planes. More specifically, an electrode or a recognition layer may be designed on the other plane of the electrochemical biosensor strip. In another embodiment, three electrodes may be designed on a plane of the strip, and the other two electrodes or a recognition layer may be designed on the other plane of the strip. Therefore, the electrodes or the recognition layer may be designed to achieve many functions, and the size of the electrochemical biosensor strip may not be increased. In addition, the volume of the sample may also not be increased.

In an embodiment of the present invention, the connector (10) includes three first type terminal components (32), two second type terminal components (34), two third type terminal components (36) and two fourth type terminal components (38) to form four front contact points and five back contact point, and two front contact points and three back contact points are designed downward, and two front contact points and two back contact points are designed upward.

In an embodiment of the present invention, the plurality of terminal components (30) is formed by a metal, the metal is bended to form two areas, the one area shows L shape, and the one area is extended from another side bending of the other area that have the contact point to another terminal. An L shape height of the first type terminal component (32) and the second type terminal component (34) are more than that of the third type terminal component (36) and fourth type terminal component (38).

Whereby, the first type terminal component (32) and the second type terminal component (34) have the downward contact point (320, 340), and the third type terminal component (36) and fourth type terminal component (38) have the upward contact point (360, 380).

In an embodiment of the present invention, an exterior corner respectively of the contact points (320, 340, 360, 380) of the terminal components (30) is a round. Further, it can plate gold on the surface of the contact points (320, 340, 360, 380). The gold plating layer can extend the life and avoid oxidising. Furthermore, the rounded exterior corner can protect the contact surface of the insertion from scratch. For example, when the insertion is an electrochemical biosensor strip, the electrodes of the electrochemical biosensor strip is not scratched easily, and the material made the electrodes will not scratch easily and then stack on the terminal component, so that the life of the terminal component can be increased and the accuracy of the terminal component can be increased.

In an embodiment of the present invention, the design of the bending area (322) is used to stagger the first type terminal component (32) and the second type terminal component (34), and then the first terminal component (32) and the second type terminal component (34) are arranged front and rear. The design of the bending area (362) is used to stagger the third type terminal component (36) and the fourth type terminal component (38), and then the third type terminal component (36) and the fourth type terminal component (38) are arranged front and rear. Further, the downward contact points (320, 340) of the first type terminal component (32) and the second type terminal component (34) are contrast corresponding to the upward contact points (360,380) of the third type terminal component (36) and the fourth type terminal component (38). Whereby, when an insertion is inserted into the connector (10), the insertion is clipped uniform by the around terminal components.

Besides, a chamfer (33) and the welding point (31) are disposed in the distal terminal of the terminal components (30). The chamfer (33) is used to enhance the soldering intensity of the terminal components (30). Compared to the prior art, the chamfer (33) may be increased the tin volume during the solder procedure, so as to enhance the soldering intensity.

In an embodiment of the present invention, the connector (10) further includes an elastic component (39). For instance, the elastic component (39) is a spring. The elastic component (39) may be assembled between the sliding base assembly opening (16) of the body (11) and the sliding base (20), so as to prop up the sliding base (20).

Figure 4:
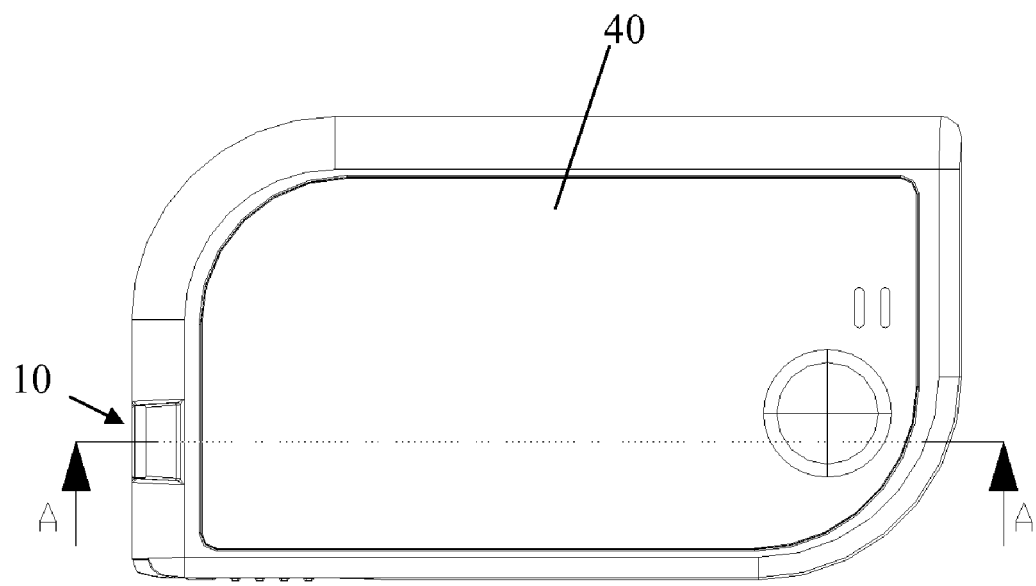
FIG. 4 is a schematic view of a biosensing meter with the connector according to an embodiment of the present invention.

Referring to FIG. 4, an embodiment of the present invention, the biosensing meter (40) can be used to measure blood glucose.

Figure 5:
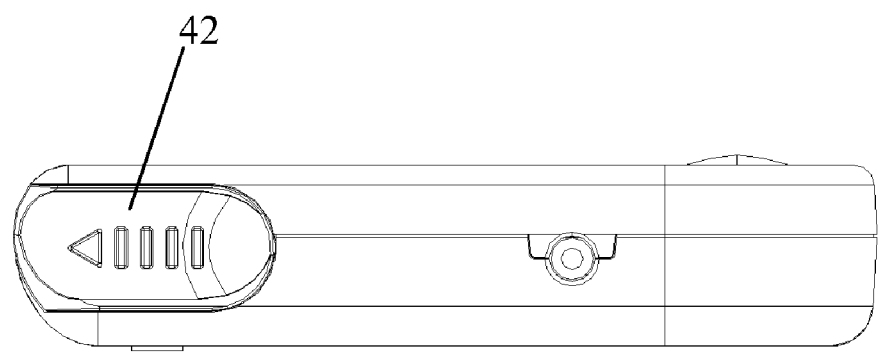
FIG. 5 is a side schematic view of the biosensing meter with an ejection component according to an embodiment of the present invention.
Figure 7A:
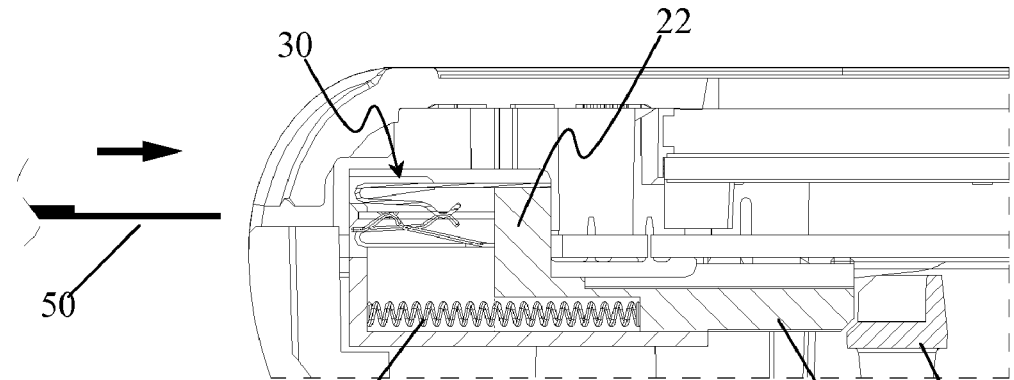
FIG. 7A to FIG. 7C are operating schematic views of an ejecting function according to an embodiment of the present invention.
Figure 7B:
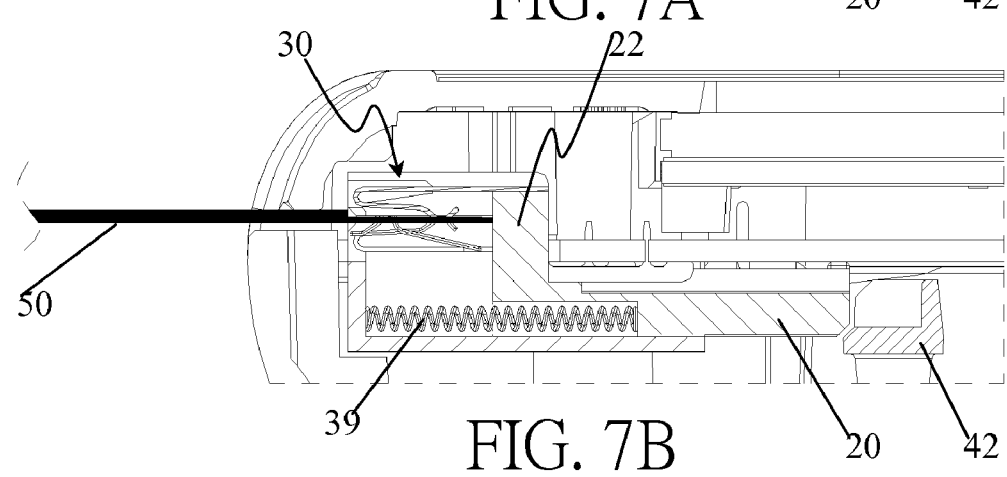
Figure 7C:
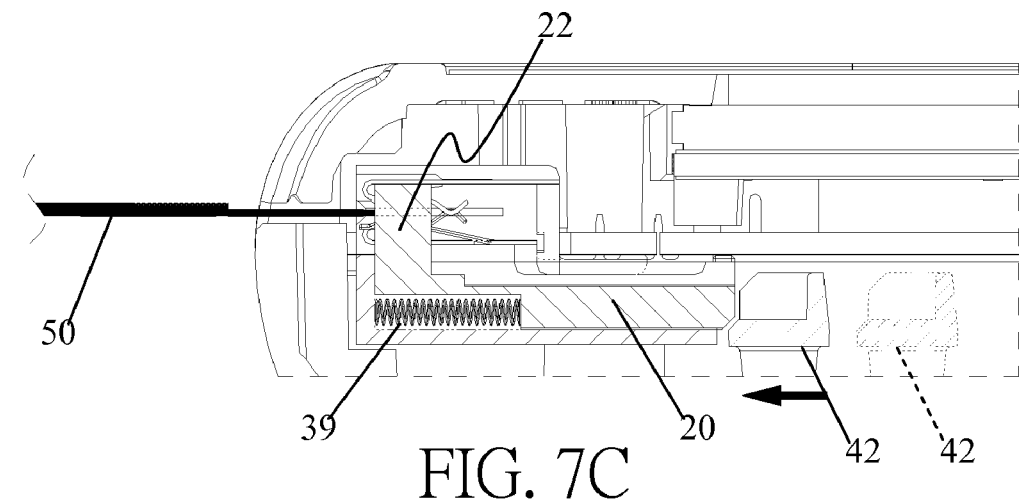

In an embodiment of the present invention, the connector (30) has an ejecting function. Referring to FIG. 5, the biosensing meter (40) includes an ejection component (42). When measuring is finished, the ejection component (42) may be used to eject the insertion out of the biosensing meter (40).

FIG. 6 shows A-A profile view of FIG. 4. Dashed area of FIG. 6 is showed in FIG. 7A to FIG. 7C. Referring to FIG. 6, and FIG. 7A to FIG. 7C, when an insertion (50) is inserted into the connector (10), the insertion (50) is clipped uniform by the around terminal components (30) (shown as FIG. 7 B). Then, the insertion (50) is used to measure. After measuring, the ejection component (42) can be pushed to drive the sliding base (20) and the pushrod (22), so as to eject the insertion (50) out of the connector (10). More specifically, the elastic component (39) can be pushed and compressed by the sliding base (20). When the ejection component (42) is released, elastic force of the elastic component (39) resets the sliding base (20) (shown as FIG. 7 A).

Figure 8A:
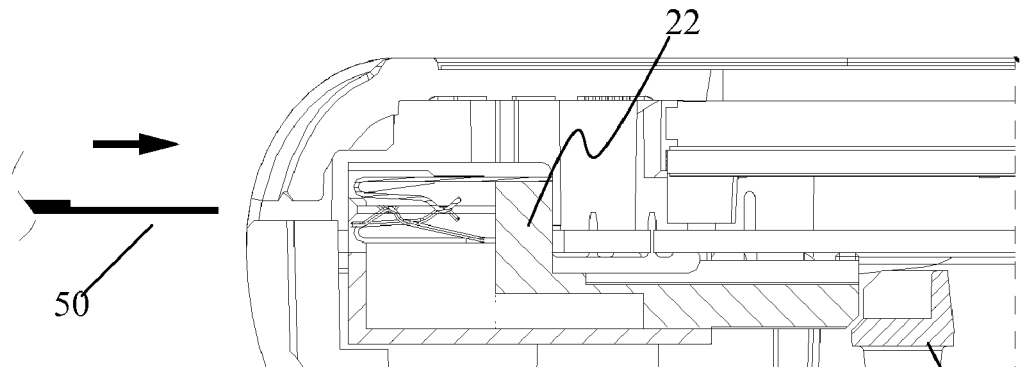
FIG. 8A to FIG. 8C are operating schematic views of an ejecting function according to another embodiment of the present invention.
Figure 8B:
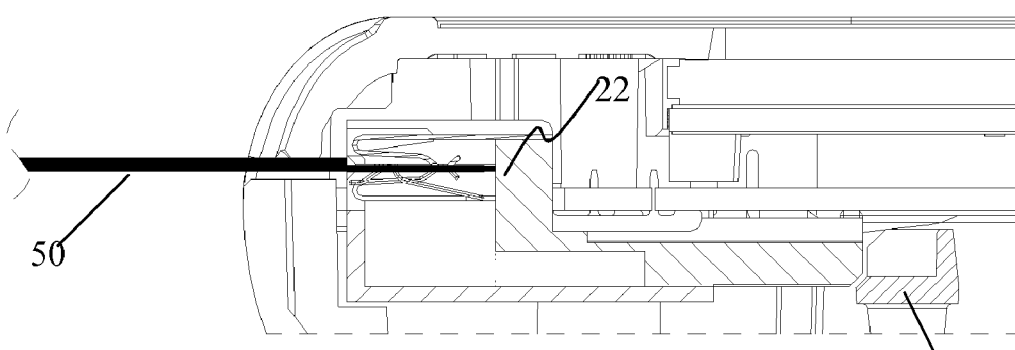
Figure 8C:
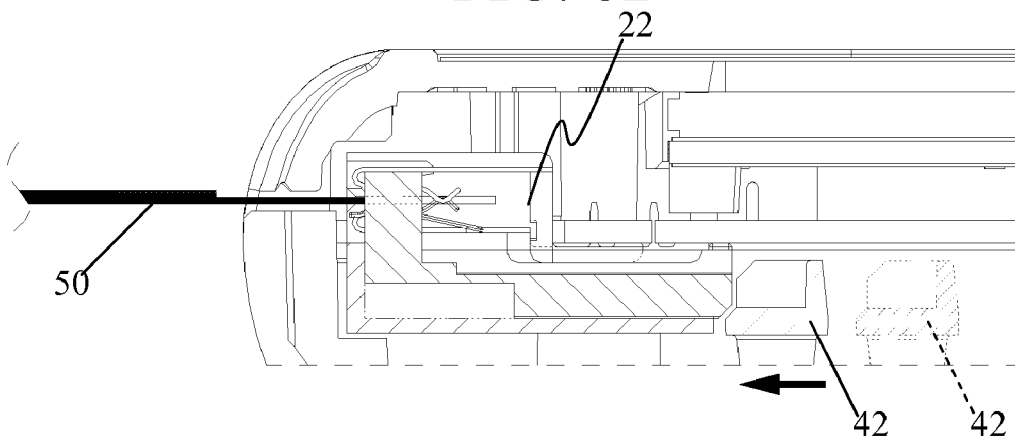

In other embodiment of the present invention, the elastic component (39) may not be included in the connector (10). Referring to FIG. 8A to FIG. 8C, when measure procedure is finished and want to eject the insertion (50), the ejection component (42) can be pushed to drive the sliding base (20), and then the insertion (50) can be ejected out of the connector (10). In the next time measuring, when a new insertion (50) is inserted into the connector (10), the new insertion (50) may push the pushrod (22) of the sliding base (20) to reset the location, and the so on the next cycle.

In summary, the connector of the present invention may have the following advantages.

1. In a connector of the present invention, in order to avoid the situation that contact terminals of the insertion are scratched easily, a plurality of terminal components showing an inverted R angle can be disposed in the connector. For instance, contact terminals of the insertion are electrodes of an electrochemical biosensor strip.

2. In a connector of the present invention, terminal components are arranged from top to bottom and from front to back. Whereby size may be reduced, the insertion may be clipped uniform, and the accuracy may be increased.

3. In a connector of the present invention, in order to increase the soldering intensity, a C angle area is located in a near terminal of the terminal components.

4. In a connector of the present invention, the contact point of the terminal components comprises a gold plating layer. The gold plating layer can extend the terminal component's life and avoid oxidising.

5. In a connector of the present invention, more terminal components can be arranged in a limited space to have more function. Furthermore, the size of the insertion may not be increased, and the volume of the sample may also not be increased.

6. In a connector of the present invention, an ejecting function can be set in the connector. Whereby, the biosensing meter does not need to include other ejecting component. In a limited space, more functions can be achieved, and the volume of the biosensing meter may be reduced.

Though the present invention has been disclosed above by the preferred embodiments, they are not intended to limit the present invention. Anybody skilled in the art can make some modifications and variations without departing from the spirit and scope of the present invention. Therefore, the protecting range of the present invention falls in the appended claims and their equivalents.

What is claimed is:

1. A connector, used in a biosensing meter and used to receive an insertion that comprises multiple electrodes, the connector comprising:
    a body, comprising a terminal assembly opening and an insertion port and having a proximal end and a distal end, wherein the terminal assembly opening is located in the proximal end of the body, and the insertion port is located in the distal end of the body and is used to receive the insertion; and
    a plurality of terminal components, assembled in the terminal assembly opening of the body, wherein each of the terminal components has a contact point, the contact point is used to contact to the electrodes of the insertion, the contact points are arranged from left to right, and the contact points are arranged from top to bottom, and the contact points are positioned with respect to the electrodes.

2. The connector according to claim 1, wherein the contact points are arranged from front to back.

3. The connector according to claim 1, further comprising a sliding base, wherein the body further comprises a sliding base assembly opening, the sliding base assembly opening is located below the terminal assembly opening, and the sliding base is slidely assembled in the sliding base assembly opening of the body.

4. The connector according to claim 3, wherein the contact points are arranged from front to back.

5. The connector according to claim 4, wherein the sliding base assembly opening is extended from the bottom of the terminal assembly opening to the top, the sliding base assembly opening includes a pushrod assembly opening located in a side of the terminal assembly opening, the sliding base includes a pushrod, and the pushrod is located on the sliding base and extended to the top and assembled in the pushrod assembly opening.

6. The connector according to claim 5, wherein the pushrod assembly opening is located two sides of the terminal assembly opening, and the sliding base comprises two pushrods, and the pushrods are respectively located in two sides of the terminal of the sliding base and assembled in the pushrod assembly opening.

7. The connector according to claim 6, wherein the sliding base assembly opening further includes a block located in appropriate inside thereof, and the sliding base includes a bump, the bump is disposed and protruding in a side of the sliding base to prop up the block of the sliding base assembly opening.

8. The connector according to claim 7, wherein two blocks are respectively located in two inner side surfaces of the sliding base assembly opening, the sliding base includes two bumps, and the bumps are respectively disposed and protruding in two sides of the sliding base.

9. The connector according to claim 8, wherein the bump is extended to outside to form a flange, and the flange is used to engage and prevent the sliding base from being separated from the body.

10. The connector according to claim 9, wherein the flange is an inclination type, the flange includes a slanting surface, and the slanting surface is used to help the sliding base be assembled into the body.

11. The connector according to claim 10, wherein a plurality of grooves are located in the terminal assembly opening, the grooves is used to assemble with the terminal components.

12. The connector according to claim 11, wherein the insertion port shows a transverse opening.

13. The connector according to claim 12, wherein a width of the transverse opening of the insertion port is less than 8.5 mm.

14. The connector according to claim 13, wherein a width of the insertion port is 8.5 mm, 7.5 mm or 7.0 mm.

15. The connector according to claim 11, wherein the contact points of the terminal components each has a round exterior corner.

16. The connector according to claim 15, wherein the terminal component comprises:
- a first type terminal component, having a terminal bended downward to form a contact point, wherein a bending area is formed in front terminal of the contact point;
- a second type terminal component, having a terminal bended downward to form a contact point;
- a third type terminal component, having a terminal bended upward to form a contact point, wherein a bending area is formed in front terminal of the contact point; and
- a fourth type terminal component, having a terminal bended upward to form a contact point.

17. The connector according to claim 16, wherein the terminal component is formed by a metal, the metal is bended to form two areas, the one area shows L shape, and the one area is extended from another side bending of the other area that have the contact point to another terminal.

18. The connector according to claim 17, wherein the terminal components include two terminal types, an L shape height of the one terminal type is more than that of the other terminal type, and the terminal components each has a proximal terminal and a distal terminal and the proximal terminal is assembled in the terminal assembly opening of the body.

19. The connector according to claim 18, wherein a chamfer is located in the distal terminal of the terminal components.

20. The connector according to claim 18, wherein the contact point comprises a gold plating layer.

21. The connector according to claim 18, wherein a welding point is disposed in the proximal terminal of the terminal component.

22. The connector according to claim 18, further comprises an elastic component, assembled between the sliding base assembly opening of the body and the sliding base.

23. The connector according to claim 18, wherein the bending area has elasticity and shows U shape.

24. The biosensing meter, comprising the connector according to claim 1.

* * * * *